United States Patent [19]

Naito et al.

[11] Patent Number: 4,935,230

[45] Date of Patent: Jun. 19, 1990

[54] HAIR WAVING AGENT

[75] Inventors: Sachio Naito; Kumi Oshima, both of Tokyo, Japan

[73] Assignee: KAO Corporation, Tokyo, Japan

[21] Appl. No.: 245,921

[22] Filed: Sep. 16, 1988

Related U.S. Application Data

[63] Continuation of Ser. No. 15,020, Feb. 17, 1987, abandoned.

[30] Foreign Application Priority Data

Mar. 3, 1986 [JP] Japan ................................. 61-45609

[51] Int. Cl.$^5$ ............................................. A61K 7/06
[52] U.S. Cl. ........................................ 424/70; 424/71; 424/72; 132/206; 132/210; 132/203; 568/50; 568/62
[58] Field of Search ................. 424/70, 71, 72; 132/7, 132/206, 210, 203; 568/50, 62

[56] References Cited

U.S. PATENT DOCUMENTS

| | | |
|---|---|---|
| 2,577,710 | 12/1951 | McDonough ....................... 132/206 |
| 2,577,711 | 12/1951 | McDonough . |
| 2,719,813 | 10/1955 | Haefele . |
| 3,394,192 | 7/1968 | Jones ..................................... 568/62 |

*Primary Examiner*—Joseph L. Schofer
*Assistant Examiner*—Peter P. Mulcahy
*Attorney, Agent, or Firm*—Oblon, Spivak, McClelland, Maier & Neustadt

[57] ABSTRACT

A novel hair waving agent comprises as its main ingredient a thioglyceryl alkyl ether or 1-phenyl-2-mercaptoethanol. The agent has low irritativeness and the good capability of wave formation.

4 Claims, No Drawings

HAIR WAVING AGENT

This is a continuation of Ser. No. 015,020, filed on 2/17/87, now abandoned.

BACKGROUND OF THE INVENTION

(1) Field of the Invention

This invention relates to a hair waving agent which has low irritativeness and the good capability of wave formation.

(2) Description of the Prior Art

The most widely used method of waving hair as desired is a permanent waving method in which a first solution for permanent waving, which contains as a principal component a reducing agent such as thioglycollic acid or cysteine, is used to open the SS linkage in the hair by reduction, thereby releasing the linkage between side chains of amino acids. This permits ready waving of the hair. Subsequently, a second solution for permanent waving comprises as its main component an oxidizing agent such as a bromate, a perborate, hydrogen peroxide or the like so that the linkage is closed by oxidation and the waved hair is fixed.

The most widely employed reducing agent used in the first permanent waving solution is thioglycollic acid. However, this acid has the disadvantages that it has inconveniently an offensive odor and gives an objectionable feel to users and is irritative. In addition, it produces great damages to hair.

A first solution using cysteine instead of the thioglycollic acid has been developed and is now in use. Although the offensive odor is reduced as compared with thioglycollic acid, cysteine is undesirably low in reducing force, so that a satisfactory degree of waving cannot be obtained. Moreover, cysteine readily suffers oxidation with air and is converted into a substance insoluble in water. This deposits on the hair or skin, thus impeding the appearance and feel or causing the skin to be chapped.

SUMMARY OF THE INVENTION

Under these circumstances in the art, the present inventors made intensive studies and, as a result, found that a high waving effect and a low irritativeness with high safety are achieved by the use of thioglyceryl alkyl ether of the following formula (I) or 1-phenyl-2-mercaptoethanol of the following formula (II):

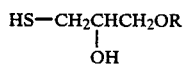
(I)

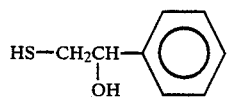
(II)

in which R represents an alkyl group having from 1 to 20 carbon atoms. The present invention was accomplished based on the above finding.

Accordingly, the present invention provides a hair waving agent which comprises as its main ingredient a thioglyceryl alkyl ether of the formula (I) or 1-phenyl-2-mercaptoethanol of the formula (II).

DETAILED DESCRIPTION OF THE INVENTION AND PREFERRED EMBODIMENTS

The compounds of the formulae (I) and (II) which are a main ingredient used in the present invention can be prepared, for example, according to a method described in Japanese Patent Application Laid-open No. 55-59160 by reaction between a glycidyl derivative and sodium hydrosulfide in the presence of carbon disulfide and an alcohol.

The hair waving agent of the invention may take a form of a first solution for a cold two-bath-type permanent agent or a form of a heating one-bath-type permanent waving agent.

The agent used as the first solution of the two bath type is prepared by dissolving from 1 to 20 wt% (hereinafter reffered to simply as %), preferably from 2 to 10%, of the thioglyceryl alkyl ether or 1-phenyl-2-mercaptoethanol in water and adjusting the pH to 4 to 11, preferably 7 to 9 by the use of a buffering agent. The treatment agent of the one bath type is prepared by dissolving from 0.1 to 5.0%, preferably from 0.5 to 3.0%, of the thioglyceryl alkyl ether or 1-phenyl-2-mercaptoethanol in water, and adjusting the pH to from 6 to 10, preferably from 7 to 9 by the use of a buffering agent.

Examples of the buffering agent include citric acid/disodium hydrogenphosphate, hydrochloric acid/sodium barbital/sodium acetate, hydrochloric acid or maleic acid/trishydroxyaminomethane, potassium or sodium dihydrogenphosphate/dipotassium or disodium hydrogenphosphate, hydrochloric acid or potassium or sodium dihydrogenphosphate/sodium tetraborate, potassium or sodium dihydrogenphosphate/sodium or potassium hydroxide, hydrochloric acid/collidine, boric acid/sodium carbonate or sodium tetraborate, hydrochloric acid/aminomethylpropandiol, glycine/sodium or potassium hydroxide, boric acid/sodium hydroxide, hydrochloric acid/sodium dimethylglycine, sodium hydrogencarbonate/sodium carbonate, sodium tetraborate/sodium hydroxide, sodium hydrogencarbonate/sodium hydroxide, water-soluble ammonium salts/ammonia, or water-soluble ammonium salts/basic amino acid. Of these, preferable combinations are those of water-soluble ammonium salts/ammonia, water-soluble ammonium salts/basic amino acids such as arginine, lysine and the like in view of the fact that such alkaline agents do rarely deposit on the hair or skin with reduced degrees of damages to hair or skin irritation. Preferable examples of the water-soluble ammonium salts include a hydrochloride, a carbonate, a bicarbonate and the like. These buffering agents are used in an amount of from 0.05 to 10%, preferably from 0.1 to 5%, of the total of the agent of the invention.

The hair waving agent may further and, in fact, preferably comprises one or more of the following materials in order to improve the waving effect and prevent damages of the hair.

(i) Peptides or their derivatives, (ii) divalent metal salts, and (iii) cationic or amphoteric polymers.

(i) Peptides and Their Derivatives (1) Peptides prepared from one or more basic amino acids (e.g. lysine, arginine) or peptides prepared from one or more acidic amino acids (e.g. glutamic acid, aspartic acid); (2) keratin proteins such as wool, feather, hooves, horns and the like, cationized products of hydrolyzates of keratin as described in Japanese Patent Application Laid-open No. 57-88111, and hydrolyzates prepared according to the method described in Japanese Patent Application Laid-open No. 57-85308 as decomposed derivatives of proteins or soybean proteins such as alubmin, globulin, conglurichinine, casein and the like; (3) naturally occurring hormones, or physiologically active peptides, e.g. insulin, oxidation-type glutathione and the like. Of these, polylysine having a molecular weight not higher than 10,000, preferably not higher than 5,000, hydrolyzates of keratin proteins and soybean proteins, and insulin are preferred.

These peptides or derivatives thereof may be used singly or in combination and are employed in an amount of from 0.01 to 50%, preferably from 0.1 to 10%, of the treatment agent of the invention.

(ii) Divalent Metal Salts

Water-soluble inorganic compounds of the following general formula $$AB_{2/m}$$

in which A represents a cation selected from the group consisting of $Ba^{2+}$, $Ca^{2+}$, $Zn^{2+}$, $Ni^{2+}$ and $Mg^{2+}$, B represents an anion selected from the group consisting of $F^-$, $Cl^-$, $Br^-$, $I^-$, $SO_4^{2-}$, $PO_4^{3-}$, $OH^-$ and $CO_3^{2-}$, and m is a valence of B, and organic salts of the above-indicated divalent metals (A) such as acetates, citrates, lactates, succinates, tertrates and the like. Of these, calcium, zinc, nickel, magnesium and barium acetates or chlorides are preferred.

The divalent metal salts may be used singly or in combination and are formulated in an amount of from 10 to 5000 ppm, preferably from 100 to 1000 ppm, as metal ions in the final form.

(iii) Cationic or Amphoteric Polymers

The following polymers, which are soluble in water in the presence or absence of inorganic or organic salts as described in Japanese Patent Application Laid-open No. 56-92812, may be mentioned.

(1) Copolymers of Acidic Vinyl Monomers and Basic Vinyl Monomers

Typical copolymers are amphoteric copolymers which are obtained by copolymerizing a monomer mixture of 45 to 55 mole% of an acidic vinyl monomer or its salt and 45 to 55 mole% of a basic vinyl monomer or its salt in the presence of a known radical polymerization initiator or in the presence or absence of a known promoter at 150° C. The molar ratio used herein is intended to mean a ratio in a case where the vinyl monomer has one acidic group or one basic group in one molecule. In the case of a monomer which has a plurality of acidic or basic groups in one molecule, the molar ratio should be suitably controlled so that the net electric charges of the respective monomers are substantially zero.

The acidic vinyl monomers should be compounds having both an acidic group such as a carboxyl group, a sulfone group, a phosphate group and the like and a polymerizable vinyl group in one molecule. Examples of such compounds include unsaturated monobasic acids such as acrylic acid, methacrylic acid, crotonic acid, vinyl benzoic acid, 2-acrylamido-2-methylpropanesulfonic acid, styrenesulfonic acid, vinylsulfonic acid, allylsulfonic acid, methallylsulfonic acid, 3-methacrylpropanesulfonic acid and the like, unsaturated dibasic acids such as itaconic acid, maleic acid, fumaric acid and the like, and monoesters thereof. The salts of these compounds include, for example, sodium salts, potassium salts, ammonium salts and the like.

The basic vinyl monomers are compounds which have a basic group such as a primary amino group, a secondary amino group, a tertiary amino group or the like and a polymerizable vinyl group in one molecule. Examples of such basic vinyl monomers include dimethylaminoethyl methacrylate, diethylaminoethyl methacrylate, dimethylaminoethyl acrylate, diethylaminoethyl acrylate, dimethylaminopropyl acrylate, dimethylaminopropyl methacrylamide, 2-vinylpyridine, 4-vinylpyridine, dimethylallylamine, diallylmethylamine and quaternarized products thereof. The quaternarized products are those compounds which may be hydrogenated products, methylated products and ethylated products and in which counter anions include, for example, a halogen ion such as a chlorine ion, a bromine ion or the like, a hydroxyl group ion, a methylsulfate group and the like.

(2) Polymers of Amphoteric Monomers

Typical amphoteric polymers are those which are obtained by polymerizing amphoteric monomers of the following general formula (III) in the present of a radical polymerization initiator at a temperature of from 20° to 120° C.

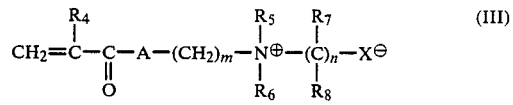

in which $R_4$, $R_7$ and $R_8$ are independently a hydrogen atom or a methyl group, $R_5$ and $R_6$ are independently a methyl group or an ethyl group, A represents —O— or —NH—, X represents —$CO_2$—$SO_3$ or —$PHO_3$, and m and n are independently an integer of from 1 to 3.

The amphoteric monomer of the general formula (III) can be prepared by reaction between a suitable aminoalkyl ester or aminoalkyl amide or acrylic acid or methacrylic acid and a lactone, a sultone or a cyclic phosphite.

Examples of these compounds include 3-dimethyl(methacroyloxyethyl)ammonium propanesulfonate, 3-dimethyl(methacroylamidopropyl)ammonium propanesulfonate and the like.

The polymerization reaction may be carried out by any known methods including, for example, bulk polymerization, aqueous solution polymerization, reversed phase suspension polymerization, precipitation polymerization and the like. The reaction smoothly proceeds at a temperature of from 20° to 150° C. in the presence of a radical polymerization initiator.

The radical polymerization initiators include, for example, sodium persulfate, potassium persulfate, ammonium persulfate, 2,2'-azobis(2-amidinopropane)dihydrochloride, benzoyl peroxide, hydrogen peroxide, sodium peracetate, cumene hydroperacetate, azobisisobutyl nitrile and the like. The amount of the radial polymerization initiator may depend on the type and is generally in the range of from 0.01 to 5% of the total monomer.

These cationic or amphoteric polymers may be used singly or in combination and are formulated in an amount of from 0.01 to 20%, preferably from 0.1 to 10%, of the hair waving treatment agent.

The hair waving treatment agent of the invention may further comprise any known additives in amounts not impeding the effect of the invention. Such additives include, for example, higher alcohols; cationic, anionic and amphoteric surface active agents; urea; silicones; aluminium compounds such as aluminium stearate, alum and the like; organic acids such as citric acid, malic acid and the like; inorganic acids such as hydrochloric acid; ethylenediamine; mono, di and triethanolamine; morpholine; basic amino acids such as arginine, lysine and the like; alkaline agents such as ammonia, caustic soda and the like; hair tonics; bactericides; colorants; perfumes and the like.

When the hair waving agent of the invention is used as a first solution for a cold two bath-type permanent waving agent, the permanent waving is conducted by a usual manner using an ordinary second solution containing oxidizing agents such as sodium bromate, potassium bromate, hydrogen peroxide and the like, at a concentration of from 1–30%, preferably 3–20%. On the other hand when it is used as a heating one bath-type permanent waving agent, the following method is used.

The agent of the invention is first applied to hair. Prior to the application of the agent, it is preferable that the hair is wound around rods, collars or a heatable handy set instrument so as to wave it in a desired form. If gentle waving is desired, an ordinary blow finishing method using a dryer or a book may be used for the waving. The amount is preferably from 10 to 150 ml for one application, which may vary depending on the conditions such as of heating. Subsequently, the hair is heated to 40° to 160° C. The heating temperature and time vary depending on the degree in which the hair is allowed to be damaged, the types of peptide and buffering solution, the pH and the preparation of the agent of the invention and the like. The healthy hair which is free of any permanent waving, hair dyeing or bleaching is treated more advantageously at higher temperatures. However, taking into account the damage of the hair by heating, the temperature is from 40° to 150° C., preferably from 40° to 80° C. In order to prevent the moisture from evaporation from the hair, it is effective to cover the hair with a cap and to moisten the hair. The heating time becomes longer at lower temperatures. For the same reasons as described above, the time is below 30 minutes, preferably from 3 to 10 minutes. On the other hand, with the hair which has been subjected to permanent waving, hair dyeing or bleaching, i.e. with chemically treated hair, it is desirable to use milder treating conditions.

The use of the hair waving agent according to the invention ensures firm waving of the hair by a simple procedure under relatively low temperature and short time conditions. Especially, the application of the waving agent of the invention to the heating one bath-type waving system is advantageous in solving the handling problems of known permanent waving agents for the following reasons. Because highly concentrated alkaline agents or reducing and oxidizing substances are not used, damages of the hair caused by elution of hair proteins can be mitigated. The agent of the invention is less irritative to the skin and has a better storage stability.

Examples are described to illustrate the invention, which should not be construed as limitation of the invention.

EXAMPLE 1

A cumulative contact enhancement test method was conducted for evaluating, sensitizing potential of reducing agents indicated in Table 1 in the guinea pig skin. The results are shown in Table 1.

TABLE 1

| Reducing Agent | Sensitizing Conditions | | Challenging Conditions | | Average* Reaction Intensity (n = 10) |
|---|---|---|---|---|---|
| | Conc. (%) | Solvent | Conc. (%) | Solvent | |
| Thioglyceryl n-butyl ether | 30 | ethanol | 100 | — | 0 |
| Thioglycollic acid | 3 | water | 30 | water | 1.6 |
| | | | 10 | " | 0.6 |
| L-cysteine | 30 | water | 60 | water | 0.3 |
| Thioglycerol | 3 | ethanol | 100 | ethanol | 2.6 |
| | | | 30 | " | 2.2 |
| | | | 10 | " | 0.8 |

*maximum score = 4.0

EXAMPLE 2

First solutions for a cold permanent waving agent having the following compositions comprising thioglyceryl alkyl ethers and 1-phenyl-2-mercaptoethanol (compounds of the invention), and thioglycollic acid and cysteine (both for control) were prepared and subjected to a cold permanent waving agent for evaluation of wave formability.

| First solution: | |
|---|---|
| reducing agent | 5.0% |
| EDTA | 0.5% |
| ammonium bicarbonate | 3.0% |
| n-propanol | 40% |
| water, ammonia solution | (pH adjusted to 9.0 by the use of ammonia aqueous solution) |
| Second solution: | |
| sodium bromate | 5.0% |
| water | 95.0% |

The healthy hair tress was wound about a rod, to which the first solution was applied, followed by rinsing with water after 3, 5, 10, 20 and 30 minutes and applying the second solution. After 10 minutes, the rod was removed and the waved hair tress was evaluated by beauty experts.

The evaluation was made according to the following evaluation standards by comparison with wave formability in known permanent waving treatments.

Evaluation Standards

⊚ strong
○ relatively strong
△ relatively weak
× weak

TABLE 2

| First Solution | Application Time (minutes) | | | | |
|---|---|---|---|---|---|
| | 3 | 5 | 10 | 20 | 30 |
| Inventive Compounds | | | | | |
| Thioglyceryl n-butyl ether | ○ | ○ | ⊚ | ⊚ | ⊚ |
| Thioglyceryl n-propyl ether | ○ | ⊚ | ⊚ | ⊚ | ⊚ |
| Thioglyceryl isopropyl ether | ○ | ⊚ | ⊚ | ⊚ | ⊚ |
| Thioglyceryl ethyl ether | ○ | ⊚ | ⊚ | ⊚ | ○ |
| Thioglyceryl methyl ether | ○ | ⊚ | ⊚ | ⊚ | ⊚ |
| Thioglyceryl n-octyl ether | △ | ○ | ○ | ⊚ | ⊚ |
| 1-Phenyl-2-mercaptoethanol | ○ | ○ | ⊚ | ⊚ | ⊚ |

TABLE 2-continued

| First Solution | Application Time (minutes) | | | | |
|---|---|---|---|---|---|
| | 3 | 5 | 10 | 20 | 30 |
| Control | | | | | |
| Thioglycollic acid | Δ | Δ | O | O | ⊚ |
| Cysteine | x | x | Δ | Δ | Δ |

By using ethanol instead of n-propanol, the first solutions having the above formulation were prepared and subjected to a cold permanent waving treatment for evaluation of wave formability. The treatment followed the above described procedure. The evaluation results obtained were the same as the ones shown in Table 2.

EXAMPLE 3

Heating one bath-type permanent waving agents indicated in Table 3 were prepared and their wave formability and retention were tested. The results are shown in Table 3.

MEASURING METHOD

Measuring Tests for a Degree of Waving and a Wave Retention (1) Ten healthy hairs of Japanese, each having a length of 15 cm, were put together and wound about a glass tube (diameter of 10 mm). These tubes were immersed in the respective treatment agents at 30° C., 50° C. and 80° C. for 20 minutes. After sufficiently rinsing with water, the hair was removed from each glass tube and was held coiled. The length of the hair coil was measured.

The degree of waving was determined according to the following equation.

Degree of waving (%) = Y/(X-Y) × 100

X: overall length of the hair (15 cm)
Y: length of the hair coil (cm)

(ii) The hair used in (i) was air-dried for one day while leaving it as suspended. Thereafter, it was gently moved for washing while immersing in an aqueous solution of 0.5% sodium laurylsulfate at 40° C. The washed hair was sufficiently rinsed and the length of the hair coil was again measured. The wave retention was determined according to the following equation.

$$\text{Wave Retention (\%)} = \frac{\text{degree of waving after washing of the hair}}{\text{degree of waving immediately after treatment}} \times 100$$

TABLE 3

| Composition Reducing Agent | pH | Conc.* (%) | Treating Temperature (°C.) | Degree of Waving (%) | Wave Retention (%) |
|---|---|---|---|---|---|
| Inventive Compounds | | | | | |
| Thioglyceryl n-butyl ether | 9.0 | 0.82 | 30 | 31 | 50 |
| " | " | " | 50 | 49 | 78 |
| " | " | " | 80 | 64 | 85 |
| Thioglyceryl n-octyl ether | 9.0 | 1.10 | 30 | 26 | 43 |
| " | " | " | 50 | 37 | 50 |
| " | " | " | 80 | 57 | 83 |
| 1-Phenyl-2-mercaptoethanol | 9.0 | 0.92 | 30 | 36 | 54 |

TABLE 3-continued

| Composition Reducing Agent | pH | Conc.* (%) | Treating Temperature (°C.) | Degree of Waving (%) | Wave Retention (%) |
|---|---|---|---|---|---|
| " | " | " | 50 | 53 | 82 |
| " | " | " | 80 | 65 | 88 |
| Control | | | | | |
| Cysteine | 9.0 | 0.6 | 30 | 20 | 32 |
| " | " | " | 50 | 30 | 44 |
| " | " | " | 80 | 53 | 76 |
| Prior cold waving agent** | — | — | 30 | 50 | 80 |

*The concentration of the SH group was determined to be at a same level for the respective reducing agents.
**First solution: 7% thioglycollic acid, pH 9.0, immersed for 10 minutes.
Second solution: 4% sodium bromate, immersed for 10 minutes.
pH adjustment: 0.2 M ammonium chloride/ammonia buffer solution.
Solvent: thioglyceryl n-butyl ether/30% n-propanol thioglyceryl n-octyl ether/30% n-propanol 1-phenyl-2-mercaptoethanol/15% n-propanol

EXAMPLE 4

Heating one bath-type permanent waving agents having the following compositions were prepared.

Composition 1

| A | thioglyceryl n-butyl ether | 2.0 (%) |
|---|---|---|
| B | n-propanol | 30.0 |
| C | hydrolyzates of keratin proteins (M.W. 630) | 1.0 |
| D | stearyl trimethylammonium chloride | 1.0 |
| E | polyoxyethylene lauryl ether (E.0. 23 moles) | 1.0 |
| F | ammonium bicarbonate | 3.0 |
| G | arginine | pH adjusted to 8.5 |
| H | perfume | 0.2 |
| I | ion-exchanged water | balance |
| | | 100.0 |

C and F were dissolved in the ion-exchanged water purged with nitrogen, to which a solution of A, D, E and H in B was added. Finally, the mixture was adjusted in pH by the use of G.

Composition 2

| A | thioglyceryl n-octyl ether | 1.5 (%) |
|---|---|---|
| B | n-propanol | 30.0 |
| C | calcium chloride | 1.0 |
| D | cetyl trimethylammonium chloride | 2.0 |
| E | ammonium chloride | 2.5 |
| F | ammonia water (28%) | pH 9.0 |
| G | perfume | 0.1 |
| H | ion-exchanged water | balance |
| | | 100.0 |

C and E were dissolved in nitrogen-purged ion-exchanged water, to which a solution of A, D and H in B was added. Finally, the pH was adjusted with F.

Composition 3

| A | 1-phenyl-2-mercaptoethanol | 2.0 (%) |
|---|---|---|
| B | cationized cellulose (commercial name Polymer JR400, by Union Carbide Co.) | 0.5 |
| C | n-propanol | 15.0 |
| D | stearyl trimethylammonium chloride | 2.0 |
| E | glycylglycine | 3.5 |
| F | lysine | pH adjusted to 9.0 |
| G | perfume | 0.2 |
| H | ion-exchanged water | balance |

-continued

| | | 100.0 |

B and E were dissolved in nitrogen-purged ion-exchanged water, to which a solution of A, D and G in C was added. Finally, the pH was adjusted with F.

Composition 4

| A | thioglyceryl n-butyl ether | 2.0 (%) |
|---|---|---|
| B | n-propanol | 30.0 |
| C | dimethylaminoethyl methacrylate-acrylamide-2-methylpropanesulfonic acid copolymer | 0.5 |
| D | sodium chloride | 3.0 |
| E | stearyl trimethylammonium chloride | 2.0 |
| F | ammonium chloride | 1.0 |
| G | ammonia water | pH adjusted to 9.0 |
| H | perfume | 0.2 |
| I | ion-exchanged water | balance |
| | | 100.0 |

C, D and F were dissolved in nitrogen-purged ion-exchanged water, to which a solution of A, E and H in B was added. Finally, the pH was adjusted with G.

What is claimed is:

1. A first solution for a two-bath-type hair waving agent comprising an aqueous solution containing
   (a) 1 to 20 wt.% of a thioglyceryl alkyl ether of the following formula (I) or 1-phenyl-2-mercaptoethanol of the following formula (II):

in which R represents an alkyl group having from 1 to 20 carbon atoms, and
   (b) 0.05 to 10 wt.% of a buffering agent selected from the group consisting of citric acid/disodium hydrogenphosphate, hydrochloric acid/sodium barbital/sodium acetate, hydrochloric acid or maleic acid/trishydroxyaminomethane, potassium or sodium dihydrogenphosphate/dipotassium or disodium hydrogenphosphate, hydrochloric acid or potassium or sodium dihydrogenphosphate/sodium tetraborate, potassium or sodium dihydrogenphosphate/sodium or potassium hydroxide, hydrochloric acid/collidine, boric acid/sodium carbonate or sodium tetraborate, hydrochloric acid/aminomethylpropandiol, glycine/sodium or potassium hydroxide, boric acid/sodium hydroxide, hydrochloric acid/sodium dimethylglycine, sodium hydrogencarbonate/sodium carbonate, sodium tetraborate/sodium hydroxide, sodium hydrogencarbonate/sodium hydroxide, water-soluble ammonium salts/ammonia, or water-soluble ammonium salts/basic amino acid, the pH of the aqueous solution being from 4 to 11.

2. A one-bath-type hair waving agent comprising an aqueous solution containing
   (a) 0.01 to 50 wt.% of a thioglyceryl alkyl ether of the following formula (I) or 1-phenyl-2-mercaptoethanol of the following formula (II):

$$HS-CH_2CHCH_2OR \atop OH \qquad (I)$$

$$HS-CH_2CH-\underset{OH}{\bigcirc} \qquad (II)$$

in which R represents an alkyl group having from 1 to 20 carbon atoms, and
   (b) 0.05 to 10 wt.% of a buffering agent selected from the group consisting of citric acid/disodium hydrogenphosphate, hydrochloric acid/sodium barbital/sodium acetate, hydrochloric acid or maleic acid/trishydroxyaminomethane, potassium or sodium dihydrogenphosphate/dipotassium or disodium hydrogenphosphate, hydrochloric acid or potassium or sodium hydrogenphosphate/sodium tetraborate, potassium or sodium dihydrogenphosphate/sodium or potassium hydroxide, hydrochloric acid/collidine, boric acid/sodium carbonate or sodium tetraborate, hydrochloric acid/aminomethylpropandiol, glycine/sodium or potassium hydroxide, boric acid/sodium hydroxide, hydrochloric acid/sodium dimethylglycine, sodium hydrogencarbonate/sodium carbonate, sodium tetraborate/sodium hydroxide, sodium hydrogencarbonate/sodium hydroxide, water-soluble ammonium salts/ammonia, or water-soluble ammonium salts/basic amino acid, the pH of the aqueous solution being from 6 to 10.

3. The hair waving agent according to claim 1 or 2, wherein said thioglyceryl alkyl ether is a thioglyceryl n-butyl ether.

4. The hair waving agent according to claim 1 or 2, wherein said thioglyceryl alkyl ether is a thioglyceryl ethyl ether.

* * * * *

UNITED STATES PATENT AND TRADEMARK OFFICE
CERTIFICATE OF CORRECTION

PATENT NO. : 4,935,230
DATED : JUNE 19, 1990
INVENTOR(S) : Saichio NAITO et al

It is certified that error appears in the above-identified patent and that said Letters Patent is hereby corrected as shown below:

Column 10, line 12, "0.01 to 50 wt.%" should read -- 0.1 to 5.0 wt.% --.

Signed and Sealed this

Twenty-eighth Day of January, 1992

Attest:

HARRY F. MANBECK, JR.

*Attesting Officer*    *Commissioner of Patents and Trademarks*